United States Patent [19]

Khanna

[11] Patent Number: 5,122,543

[45] Date of Patent: Jun. 16, 1992

[54] ORAL FORMS OF ADMINISTRATION WITH DELAYED RELEASE

[75] Inventor: Satish C. Khanna, Bottmingen, Switzerland

[73] Assignee: Ciba-Geigy Corporation, Ardsley, N.Y.

[21] Appl. No.: 453,103

[22] Filed: Dec. 14, 1989

Related U.S. Application Data

[63] Continuation of Ser. No. 186,839, Apr. 27, 1988, abandoned.

[30] Foreign Application Priority Data

May 4, 1987 [CH] Switzerland .......................... 1682/87

[51] Int. Cl.$^5$ ...................... A01N 43/46; A61K 31/79
[52] U.S. Cl. .................... 514/772.5; 514/217
[58] Field of Search ............... 424/80; 514/217, 772.5

[56] References Cited

U.S. PATENT DOCUMENTS

| | | | |
|---|---|---|---|
| 2,861,920 | 11/1958 | Dale et al. | 424/78 |
| 4,213,963 | 7/1980 | Mesens et al. | 424/80 |
| 4,409,212 | 10/1983 | Mondadori | 424/244 |
| 4,632,843 | 12/1986 | Pich et al. | 514/951 |
| 4,857,336 | 8/1989 | Khanna et al. | 424/473 |

FOREIGN PATENT DOCUMENTS 2950476 12/1977 Fed. Rep. of Germany .
4537557 7/1968 Japan .

OTHER PUBLICATIONS

Chem. Abstract vol. 101: 198028k.
Kala et al., Pharmazie vol. 41, No. 1, pp. 61–62 (1986).
CA 74: 79592d (1971).
CA 95: 121077a (1981).

*Primary Examiner*—Thurman K. Page
*Assistant Examiner*—Peter F. Kulkosky
*Attorney, Agent, or Firm*—Irving M. Fishman; Karen G. Kaiser

[57] ABSTRACT

The present invention relates to improved oral forms of administration, for example syrups, having a delayed release characteristic, of carbamazepine. The delayed release of carbamazepine is achieved by the manufacture of an advantageous cubic crystal form of suitable size of dihydrate crystals contained in the form of administration.

3 Claims, No Drawings

ORAL FORMS OF ADMINISTRATION WITH DELAYED RELEASE

This application is a continuation of application Ser. No. 186,839, filed Apr. 27, 1988, now abandoned.

The present invention relates to oral forms of administration for carbamazepine in the form of stable aqueous suspensions having a delayed release characteristic, processes for the manufacture of these oral forms of administration and their use as analgesics and/or anticonvulsants.

Carbamazepine, 5H-dibenz[b,f]azepine-5-carboxamide (Tegretol ®, Tegretal ®: Ciba-Geigy) is designated as an anticonvulsant and as an analgesic. Commercially available forms of administration are tablets containing 200 mg of active ingredient and syrups with an active ingredient content of 2%. In general, liquid oral forms of administration, such as syrups, have certain advantages over tablets; for example they are easier to take (taste better) and the dosage can be varied. For those reasons syrups are suitable especially for children.

At the start of treatment with carbamazepine there may be occasional side-effects such as loss of appetite, dryness of the mouth, nausea, diarrhoea, constipation, headaches, dizziness, drowsiness, ataxia, hypocyclosis, diplopia, etc., see Schweizer Arzneimittelkompendium 1987, p. 1581 ff., Volume 1, Documed Basle.

In the case of the commercially available syrup these unfavourable side-effects can be attributed to the high concentration of active ingredient in the plasma after the syrup has been taken. Maximum active-ingredient concentrations in the plasma are reached after from ½ hour to 3 hours, see Schweizer Arzneimittelkompendium, loc. cit. The rapid absorption of the active ingredient is due to the fineness of the carbamazepine crystals in the syrup: It is known that in the case of sparingly soluble active ingredients the dissolution rate and hence the absorption and passage into the blood may be increased if the form of administration in question contains especially small particles of active ingredient, see in this respect R. Voigt, Lehrbuch der Pharmazeutischen Technologie, Verlag Chemie, referred to hereinafter as "Voigt", bottom of page 636 (28.5.2.1): "The particle size thus assumes central importance, since with its reduction and the resulting increase in the specific surface area it is possible to achieve an increase in the dissolution rate and, as a function thereof, an increase in the absorption."

The commercially available syrup contains needle-shaped carbamazepine hydrate crystals having a particle size of less than 10 μm. The presence of carbamazepine hydrate crystals having a small particle size can be explained by the method of manufacture of the syrup:

It is known, see J. Pharm. Soc. Jpn. No. 2, 184–190, 1984, that in contact with water anhydrous carbamazepine (amorphous or crystalline) forms a dihydrate. This dihydrate is in the form of needle-shaped crystals which can grow to a particle size of approximately from 100 to 500 μm in the longitudinal direction. As a rule, needle-shaped crystals, and needle-shaped crystals of that size in particular, are difficult to suspend because of their flocculation characteristics and/or their tendency to sedimentation, with the result that an aqueous suspension of dihydrate crystals is produced in a separate process step, using anhydrous carbamazepine as starting material. The needle-shaped crystals must then be ground wet, for example in a colloid mill. During the grinding operation it is not possible to prevent some of the ground material from consisting of fragments having a particle size of less than 10 μm, the proportions varying according to the duration and intensity of the grinding.

Hitherto only the wet grinding process has been suitable for comminuting the large needle-shaped dihydrate crystals, since for dry grinding processes the material that is to be ground has itself to be dried. There are problems with the drying in the case of dihydrate crystals of carbamazepine, since anhydrous carbamazepine is formed again in the process. Until now, therefore, the only liquid oral forms of administration of carbamazepine that have been available are those made from wet ground needle-shaped dihydrate crystals.

The problem on which the present invention is based is to manufacture improved oral forms of administration for carbamazepine in the form of stable aqueous suspensions having a delayed release characteristic.

This problem is solved by the present invention which relates to oral forms of administration for carbamazepine containing carbamazepine dihydrate crystals of a shape suitable for stable suspensions, for example cubic or cuboid, and a minimum particle size suitable for delayed release, for example larger than approximately 10 μm and smaller than approximately 200 μm.

In the context of the description of the present invention the general definitions and terms used hereinbefore and hereinafter preferably have the following meanings:

Oral forms of administration for carbamazepine are, for example, drops and especially syrups.

In a stable aqueous suspension the carbamazepine dihydrate crystals are in the dispersed form for from several days to several weeks without the premature formation of sediments of active ingredient crystals being observed.

The particle size of dihydrate crystals suitable for the delayed release of carbamazepine is in the range of from more than approximately 10 μm to approximately 200 μm. The preferred range is the range above approximately 20 μm and below approximately 100 μm. At least 90% of the dihydrate crystals are in the range of from approximately 10 μm to approximately 200 μm and at least 80% of the dihydrate crystals are in the range of from approximately 20 μm to approximately 100 μm.

The particle size indicates an approximate value, which can be ascertained by measuring the diameter of carbamazepine dihydrate crystals. Suitable for determining that value are the known methods of particle-size analysis, for example microscopic methods using a light microscope; particle-size measurement using light, for example light scatter methods or turbidimetric methods; sedimentation methods, for example pipette analysis using an Andreasen pipette, a sedimentation balance, a photo sedimentometer or sedimentation in the centrifugal force field; impulse methods, for example using a Coulter Counter, or sizing using gravity or centrifugal force. These methods are described inter alia in Voigt on pages 64–79.

The particle size is preferably ascertained from a sample of dihydrate crystals by first making a representative selection, for example 90% of the crystals from a sample, eliminating especially large and small crystals, and, using one of the mentioned methods, ascertaining from this sample, from which crystals of extreme sizes have been eliminated, a mean particle diameter with standard deviation. With the particle sizes indicated the positive and negative standard deviation is approximately from 1 to 10% of the mean value.

The oral forms of administration for carbamazepine according to the invention are distinguished by being especially well tolerated and having good storage stability. For example in the case of syrups no sedimentation of active ingredient crystals is observed over relatively long periods of weeks and months. It is especially surprising that no formation or agglomeration of needle-shaped dihydrate crystals can be observed in these liquid forms of administration which could adversely affect the flow properties and hence the dosage. The delayed release of the active ingredient from crystals of a particle size of more than 10 μm, especially more than 20 μm, brings about especially uniform absorption of the active ingredient and effectiveness of a therapeutic level, while avoiding the high initial dose.

The oral forms of administration according to the invention are prepared by making an aqueous dispersion using a suitable protective colloid which influences the growth in water of carbamazepine hydrate forms of suitable shape and size and adding anhydrous carbamazepine to this dispersion and processing the resulting suspension further to liquid oral forms of administration.

This process has substantial advantages, for example the fact that oral forms of administration such as syrups can be manufactured in which an especially high proportion of the active ingredient, for example more than 90% carbamazepine dihydrate, is of cubic or cuboid form and is in the advantageous particle-size range of from more than approximately 10 μm up to 200 μm, and that, especially, the wet grinding process, which has proved technically complicated and, because of the formation of particles smaller than 10 μm, disadvantageous, can be avoided.

The term "aqueous dispersion" includes aqueous phases in which the protective colloid is in suspended, colloidal-dispersion or dissolved form, depending on its solubility in water.

The anhydrous carbamazepine which is used to produce the aqueous suspension with the formation of the hydrate forms preferably consists of amorphous or crystalline forms of any desired particle size.

Protective colloids that influence the growth of carbamazepine hydrate forms, especially of cubic or cuboid dihydrate crystals, prevent the formation of hydrate crystals, especially dihydrate crystals, having a particle size of more than 200 μm. In particular such protective colloids, surprisingly, promote the formation of cubic or cuboid shapes and inhibit the formation of disadvantageous crystal shapes that are unsuitable for the production of suspensions, for example relatively large needle-shaped dihydrate crystals. As mentioned hereinbefore, the formation of relatively large needle-shaped dihydrate crystals from anhydrous modifications or amorphous particles is disadvantageous for the production of suspensions since the needle-shaped crystals tend to form agglomerates and have a tendency towards sedimentation and therefore have to be ground wet. In addition, suspensions with needle-shaped dihydrate crystals have poor flow characteristics.

Such protective colloids are especially water-soluble polymers of aliphatic or cyclic vinyl amides, for example poly-N-vinyl-methylacetamide, -ethylacetamide, -methylpropionamide, -ethylpropionamide, -methylisobutyramide, -2-pyrrolidone, -2-piperidone, -epsilon-caprolactam, -5-methyl-2-pyrrolidone or -3-methyl-2-pyrrolidone, especially poly-N-vinylpyrrolidone having a mean molecular weight of approximately 10,000–360,000, or copolymers of the mentioned water-soluble polymers of aliphatic or cyclic vinyl amides, for example poly-N-vinylpyrrolidone, with water-soluble polyvinyl acetate or polyvinyl alcohol of varying acetate content, for example polyvinyl acetate having a molecular weight of approximately from 5,000 to 400,000 or polyvinyl alcohol of a degree of hydrolysis of approximately 85–98% and a degree of polymerisation of approximately 500–2,500.

Suitable protective colloids are especially adjuvants, such as poly-N-vinylpyrrolidone, having a mean molecular weight of approximately from 2,500 to 360,000, for example Kollidon ® (BASF), Plasdone ®, Peristone ® (General Aniline) or Luviskol ® (BASF), and having the following characteristics:

soluble in water, ethanol, methanol, isopropanol, glycerol, propylene glycol, methylene chloride, insoluble in ether, hydrocarbons, strongly hygroscopic (water absorption approximately 33% from approximately 70% relative humidity), see Pharmazeutische Technologie, Sucker H. et al., Thieme Verlag, Stuttgart 1978, page 339.

Also preferred is the vinylpyrrolidone/vinyl acetate copolymer having a monomer ratio of vinylpyrrolidone to vinyl acetate of approximately 60:40 (% by weight) and having the following characteristics:

purity: 95% (remainder water), insoluble in ether, aliphatic hydrocarbons, very readily soluble in water, ethyl and isopropyl alcohol, methylene chloride, glycerol and 1,2-propylene glycol, pH value of a 10% aqueous solution: 3–5, viscosity (10% aqueous solution): 5 mPas, see H. P. Fiedler, Lexikon der Hilfsstoffe, Editio Cantor 1982.

Vinylpyrrolidone/vinyl acetate copolymers are known and/or can be manufactured in a manner known per se in any desired mixing ratio of the monomers. The preferred 60:40 copolymer is commercially available, for example under the name Kollidon ® VA 64 (BASF).

The oral forms of administration according to the invention are preferably manufactured by dispersing a specific amount of the protective colloid in a predetermined volume of water, so that at first an approximately 0.1–20%, preferably an approximately 1.0–5.0%, aqueous dispersion is obtained, optionally sterile-filtering the dispersion, and adding the desired amount of carbamazepine (anhydrous). The suspension can then be stirred under mild conditions, preferably at from 5° to approximately 80°, and processed further to liquid oral forms of administration.

Cubic or cuboid dihydrate crystals having an average particle size larger than approximately 10 μm and smaller than approximately 200 μm are formed in the aqueous suspension. With this method a proportion of more than 90% of crystals having this advantageous particle size can be formed.

In the further processing of the suspension to oral forms of administration, especially syrups, the customary pharmaceutical methods, such as those described, for example, in Hagers Handbuch der Pharmazeutischen Praxis, Springer Verlag 1971, Volume VII, Section A, pages 640–644, or in Remington's Pharmaceutical Sciences, Mack 1985, pages 1500–1503, are used.

During that further processing there may be added to the aqueous suspension containing the carbamazepine dihydrate crystals and protective colloids other adjuvants suitable for oral formulations, such as substances that increase the viscosity, wetting agents, preservatives, anti-oxidants, colourings, flavourings (aromatic substances), sugars and/or sweeteners (syrup base). It is, however, also possible for the carbamazepine dihydrate crystals to be separated from the protective colloid by filtration. The carbamazepine dihydrate crystals in the advantageous particle-size range of from approximately 10 μm to 200 μm are then resuspended in water. The adjuvants can then be added to this suspension. It is, however, possible alternatively to suspend the filtered dihydrate crystals in the syrup base.

Substances that increase the viscosity are, for example, inorganic stabilisers of suspensions, for example colloidal silicates containing a large proportion of aluminium and magnesium, such as bentonites, Veegum or Gelwhite, colloidal silicic acid, for example Aerosil ® (Degussa), Cabosil ® (Cabot), organic stabilisers, for example swelling agents such as alginates, for example sodium alginate, potassium alginate or propylene glycol alginate, gum arabic, tragacanth, karaya gum, sterculia gum, carageenan, guar gum or agar, synthetic or semi-synthetic swelling agents, for example 1,2-epoxy polymers, especially ethylene oxide homopolymers having a degree of polymerisation of approximately 2,000–100,000, which are known, for example, under the trade name Polyox ® (Union Carbide), swellable cellulose ethers, for example methyl- or ethyl-cellulose, hydroxypropylcellulose, hydroxypropylmethylcellulose, methyl- or ethyl-hydroxyethylcellulose, hydroxyethylcellulose or carboxymethylcellulose, microcrystalline cellulose or additional amounts of polyvinylpyrrolidone.

Suitable wetting agents are, for example, sulpho-succinates, such as dihexyl, dioctyl or diamyl sulphosuccinate; sulphonates or sulphates, for example sodium alkylnaphthalene sulphonate, fatty alcohol sulphonates or fatty alcohol polyglycol ether sulphates; fatty acid polyglycol esters, for example polyethylene glycol stearates, polyglycol esters of $C_8$–$C_{18}$-fatty acids; fatty alcohol polyglycol ethers, for example lauryl, cetyl, stearyl or oleoyl alcohol polyglycol ether or cetylstearyl alcohol polyglycol ether; poly-fatty acid ester polyglycol ethers, for example polyethylene glycol sorbitan monolaurate, monopalmitate, monostearate or monooleate, glycerin fatty acid ester polyglycol ethers or pentaerythritol fatty acid polyglycol ethers; saccharose esters, for example saccharose mono- and di-stearate or saccharose monopalmitate; ethoxylated vegetable oils, for example ethoxylated castor oil or hydrogenated and ethoxylated castor oil, or block polymers, such as polyoxyethylene/polyoxypropylene polymers.

Suitable preservatives are, for example, benzoic acid, sodium benzoate, sorbic acid, for example sodium or potassium sorbate, p-hydroxybenzoic acid methyl ester or p-hydroxybenzoic acid propyl ester (Parabens) or chlorohexidine diacetate or digluconate.

Suitable antioxidants are, for example, ascorbic acid, ascorbyl palmitate, propyl gallate, nordihydroguaiaretic acid (NDGA), butylhydroxytoluene (BHT) or tocopherols, optionally in admixture with synergists, such as ascorbic acid, citric acid, citraconic acid, phosphoric acid or tartaric acid.

Colourings can be used to enhance the appearance of the preparation and to identify the preparation. Suitable colourings that are permitted in pharmacy are, for example, indigotin (I) (blue), amaranth (red), yellow orange S (orange) or tartrazine XX (yellow).

Sugars and sweeteners which can be used as the syrup base are, for example, saccharose, xylitol, D-xylose, maltose, D-glucose, sorbitol, glycerol, mannitol, dulcitol or lactose and sodium saccharin, dulcin, ammonium glycyrrhizinate or sodium cyclamate.

The oral forms of administration according to the invention have valuable pharmacological properties and can therefore be used in the treatment of severe pain and convulsions of various geneses, for example in the treatment of epilepsy. The invention relates also to the use of these oral forms of administration for the treatment of such conditions, especially epilepsy.

EXAMPLE 1 a) Manufacture of an Active Ingredient Preparation 1.0 g of vinylpyrrolidone/vinyl acetate copolymer (Kollidon ® VA 64-BASF) is dissolved in 100 ml of deionised water and 10.0 g of anhydrous carbamazepine are added to the solution. The active ingredient is dispersed by stirring the suspension. Cubic and cuboid dihydrate crystals having a particle size of approximately 10–200 μm are formed.

b) Manufacture of a Syrup

The following adjuvants are added to the suspension obtainable according to a):

| | |
|---|---|
| microcrystalline cellulose (Avicel ® RC 59) | 5.00 g |
| sodium carboxymethylcellulose | 1.00 g |
| sodium saccharin | 1.00 g |
| methylparaben | 0.60 g |
| propylparaben | 0.20 g |
| deionised water ad | 500.00 ml |

The syrup can then be introduced into 50 ml or 100 ml bottles.

EXAMPLE 2

Analogously to Example 1a), aqueous suspensions containing 10 g of carbamazepine dihydrate crystals are prepared by adding to the carbamazepine dihydrate 2.0 g of poly-N-vinylpyrrolidone (Kollidon ® K-30 or Kollidon ® K-90), or 1.0 g of vinylpyrrolidone/vinyl acetate copolymer (Kollidon ® VA 64) and 0.5 g of polyethylene glycol having a degree of polymerisation of approximately 2,000–100,000 or 2.0 g of poly-N-vinylpyrrolidone (Kollidon ® K-30 or Kollidon ® K-90) and 0.5 g of polyethylene glycol having a degree of polymerisation of approximately 2,000–100,000; these suspensions can be used for the manufacture of syrups.

I claim:

1. An aqueous suspension in the form of a syrup suitable for the oral administration of carbamazepine which exhibits improved delayed release characteristics and improved stability comprising carbamazepine dihydrate crystals having cubic or cuboidal shape and a particle size from approximately 10μ to approximately 200μ and wherein said crystals are no larger than 200μ obtained by dispersing in water an effective amount of anhydrous carbamazepine, and an effective amount of a polyvinylpyrrolidone/vinylacetate copolymer as protective colloid and pharmaceutically acceptable adjuvants.

2. An aqueous suspension according to claim 1, wherein the vinylpyrrolidone/vinylacetate copolymer has a monomer ratio of vinylpyrrolidone to vinylacetate of approximately 60:40 (% by weight).

3. A process for the preparation of an aqueous suspension in the form of a syrup for the oral administration of carbamazepine according to claim 1 which comprises dispersing in a predetermined amount of water a vinylpyrrolidone/vinylacetate copolymer as protective colloid, adding an effective amount of anhydrous carbamazepine and processing this dispersion further to oral forms of administration.

* * * * *